(12) United States Patent
Jochinsen et al.

(10) Patent No.: US 10,864,054 B2
(45) Date of Patent: Dec. 15, 2020

(54) TRI-AXIAL ERGONOMIC FOOTSWITCH

(71) Applicant: NOVARTIS AG, Basel (CH)

(72) Inventors: Mauricio Jochinsen, Fountain Valley, CA (US); Fred Mercado, Laguna Hills, CA (US); Lingfeng Yu, Rancho Santa Margarita, CA (US)

(73) Assignee: Alcon Inc., Fribourg (CH)

( * ) Notice: Subject to any disclaimer, the term of this patent is extended or adjusted under 35 U.S.C. 154(b) by 533 days.

(21) Appl. No.: 15/807,710

(22) Filed: Nov. 9, 2017

(65) Prior Publication Data

US 2018/0132958 A1 May 17, 2018

Related U.S. Application Data

(60) Provisional application No. 62/500,176, filed on May 2, 2017, provisional application No. 62/423,272, filed on Nov. 17, 2016.

(51) Int. Cl.
*A61B 34/00* (2016.01)
*G05G 9/047* (2006.01)
(Continued)

(52) U.S. Cl.
CPC ............... *A61B 34/74* (2016.02); *G05G 1/38* (2013.01); *G05G 1/40* (2013.01); *G05G 1/44* (2013.01); *G05G 9/04* (2013.01); *G05G 9/04788* (2013.01); *G06F 3/0334* (2013.01); *G16H 40/63* (2018.01); *A61B 17/00* (2013.01); *A61B 90/06* (2016.02); *A61B 2017/00973* (2013.01);
(Continued)

(58) Field of Classification Search
CPC .......... A61B 34/74; A61B 2017/00973; G05G 1/38; G05G 1/40; G05G 1/44; G06F 3/0334
See application file for complete search history.

(56) References Cited

U.S. PATENT DOCUMENTS 5,583,407 A * 12/1996 Yamaguchi ........... A63F 9/0291
273/375
5,635,777 A 6/1997 Telymonde et al.
(Continued)

FOREIGN PATENT DOCUMENTS

DE         4336153 C1 *  3/1995 ........... G06F 3/0334
WO    2016/042407 A1     3/2016

OTHER PUBLICATIONS

Trombley, Donald J., "Experimental Determination Of An Optimal Foot Pedal Design" Thesis, submitted to Graduate Faculty of Texas Technological College, 1966, 72 pages.
(Continued)

*Primary Examiner* — Vicky A Johnson

(57) ABSTRACT

A foot-operated controller includes a base configured to rest on a floor surface, and a movable contact surface coupled to the base. The contact surface includes an anterior region to support a toe region and a posterior region to support a heel region, and is configured to roll about a roll axis in response to inversion or eversion of a foot engaged with the contact surface, pitch about a pitch axis in response to plantar flexion or dorsiflexion of the foot, and yaw about a yaw axis in response to abduction or adduction of the foot. The roll, pitch, and yaw axes intersect at a point superior to the contact surface, and may align with the operator's ankle.

5 Claims, 4 Drawing Sheets

(51) Int. Cl.
*G05G 1/40* (2008.04)
*G06F 3/033* (2013.01)
*G16H 40/63* (2018.01)
*G05G 1/38* (2008.04)
*G05G 1/44* (2008.04)
*G05G 9/04* (2006.01)
*A61B 17/00* (2006.01)
*A61B 90/00* (2016.01)
*A61F 9/008* (2006.01)

(52) U.S. Cl.
CPC ............... *A61B 2017/00977* (2013.01); *A61B 2034/742* (2016.02); *A61B 2090/061* (2016.02); *A61B 2090/065* (2016.02); *A61B 2090/067* (2016.02); *A61F 9/008* (2013.01)

(56) References Cited

U.S. PATENT DOCUMENTS

| | | | |
|---|---|---|---|
| 5,787,760 A | 8/1998 | Thorlakson | |
| 6,179,829 B1 | 1/2001 | Bisch et al. | |
| 6,452,120 B1* | 9/2002 | Chen | G05G 1/30 200/52 R |
| 6,659,998 B2 | 12/2003 | Dehoogh et al. | |
| 6,862,951 B2 | 3/2005 | Peterson | |
| 6,962,581 B2 | 11/2005 | Thoe | |
| 7,012,203 B2 | 3/2006 | Hanson et al. | |
| 7,019,234 B1 | 3/2006 | Mezhinsky | |
| 7,084,364 B2 | 8/2006 | Mezhinsky | |
| 7,185,555 B2 | 3/2007 | Peterson | |
| 7,193,169 B2 | 3/2007 | Mezhinsky | |
| 7,381,917 B2 | 6/2008 | Dacquay | |
| 7,531,006 B2 | 5/2009 | Clausen | |
| 7,619,171 B2 | 11/2009 | Horvath et al. | |
| 7,626,132 B2 | 12/2009 | Mezhinsky | |
| 8,048,094 B2 | 11/2011 | Finlay | |
| 8,319,125 B2 | 11/2012 | Jo et al. | |
| 8,657,886 B2 | 2/2014 | Clausen | |
| 8,680,412 B2 | 3/2014 | Horvath | |
| 8,911,447 B2 | 12/2014 | Van Der Walt | |
| 9,114,030 B2 | 8/2015 | Dastous | |
| 9,240,110 B2 | 1/2016 | Roth | |
| 9,386,918 B2 | 7/2016 | Ammari et al. | |
| 9,456,769 B2 | 10/2016 | Stein | |
| 2003/0214483 A1 | 11/2003 | Hammer et al. | |
| 2006/0145540 A1 | 7/2006 | Mezhinsky | |
| 2006/0156903 A1 | 7/2006 | Baird et al. | |
| 2007/0043339 A1* | 2/2007 | Horvath | A61F 9/008 606/2 |
| 2008/0318679 A1 | 12/2008 | Tran et al. | |
| 2010/0060614 A1 | 3/2010 | Enns | |
| 2010/0230259 A1* | 9/2010 | Jo | G05G 1/30 200/86.5 |
| 2014/0031123 A1* | 1/2014 | Sarrafzadeh | G06F 3/0334 463/36 |
| 2015/0173725 A1* | 6/2015 | Maxson | A61B 17/00 606/1 |
| 2016/0320862 A1 | 11/2016 | Schradin | |
| 2016/0321947 A1 | 11/2016 | Toronto | |
| 2018/0132948 A1 | 5/2018 | Mercado | |
| 2019/0354200 A1 | 11/2019 | Rapoport | |
| 2019/0354201 A1 | 11/2019 | Rapoport | |
| 2020/0064879 A1 | 2/2020 | Jawidzik | |
| 2020/0085515 A1 | 3/2020 | Jawidzik | |

OTHER PUBLICATIONS

Wootten, D. and Hull, M., "Design and Evaluation of a Multi-Degree-of-Freedom Foot/Pedal Interface for Cycling", International Journal of Sport Biomechanics, 1992, 8, 152-164 pages.

* cited by examiner

TRI-AXIAL ERGONOMIC FOOTSWITCH

This application claims benefit of and priority from U.S. provisional application Ser. No. 62/500,176 titled "Tri-Axial Ergonomic Footswitch", filed May 2, 2017, and U.S. provisional application Ser. No. 62/423,272 titled "Ergonomic Foot-Operated Joystick", filed Nov. 17, 2016, the disclosures of which are hereby incorporated by reference in their entirety.

FIELD

The present disclosure relates generally to device controllers, and more particularly to foot-operated controllers.

BACKGROUND

During ophthalmic surgery, a surgeon may utilize foot-operated controls to manipulate surgical equipment while the surgeon's hands are actively involved in performing the surgery. For example, the surgeon may control an imaging, light, fluid flow, suction, rotation, and/or focus using the foot-operated controller, such as a footswitch. Conventional foot controllers respond to movements about one or two axes of movement aligned at or below the bottom of the operator's foot. There is an automatic reaction of the upper body when a person in a sitting position moves his foot or leg. The body may compensate for changes in position and weight distribution by reacting (often unconsciously) to maintain balance. As a result, foot and leg movements during a surgical procedure can impact balance and can make it difficult to maintain steady hands and head. Accordingly, there is a need for such a foot controller to be ergonomically designed to facilitate stability of the head and hands during surgical procedures.

SUMMARY

Certain embodiments include a foot-operated controller comprising a base configured to rest on a floor surface, a movable contact surface coupled to the base, the movable contact surface comprising an anterior region to support a toe region and a posterior region to support a heel region. The movable contact surface may be configured to roll about a roll axis in response to inversion or eversion of a foot engaged with the contact surface, pitch about a pitch axis in response to plantarflexion or dorsiflexion of the foot, and yaw about a yaw axis in response to abduction or adduction of the foot. The controller may include a roll sensor coupled to the foot-operated controller and configured to detect a roll of the contact surface and send a signal indicating the detected roll to a microprocessor, a pitch sensor communicatively coupled to the foot-operated controller and configured to detect a pitch of the contact surface and send a signal indicating the detected pitch to the microprocessor, and a yaw sensor communicatively coupled to the foot-operated controller and configured to detect a yaw of the contact surface and send a signal indicating the detected yaw to the microprocessor.

In certain embodiments, the roll axis is located in a roll plane superior to the contact surface. The roll, pitch and yaw axes may intersect at a point superior to the contact surface. For example, the roll, pitch and yaw axes intersect at a point located 1-30 millimeters above the contact surface. In certain examples, the roll, pitch and yaw axes intersect at a point aligned with to an ankle moving the foot. Additionally, a point at which the roll, pitch, and yaw axes intersect may be adjustable.

Certain variants include a method of operating a foot-operated controller which comprises engaging a foot with a movable contact surface of the foot-operated controller, inverting or everting the foot to cause the contact surface to roll about a roll axis, thereby controlling a first function of a medical device, plantarflexing or dorsiflexing the foot to cause the contact surface to pitch about a pitch axis, thereby controlling a second function of the medical device, abducting or adducting the foot to cause the contact surface to yaw about a yaw axis, thereby controlling a third function of the medical device.

Certain variants include a non-transitory computer-readable medium storing instructions that, when executed, cause a processor to receive a signal indicating a roll about a roll axis of a contact surface of a foot-operated controller, determine a change in roll position associated with the roll, and generate a first signal to control a first function of a medical device based on the determined change in roll position. The instructions, when executed, may further cause the processor to receive a signal indicating a pitch about a pitch axis of the contact surface of the foot-operated controller, determine a change in pitch position associated with the pitch, and generate a second signal to control a second function of the medical device based on the determined change in pitch position. The instructions, when executed, may further cause the processor to receive a signal indicating a yaw about a yaw axis of the contact surface of the foot-operated controller, determine a change in yaw position associated with the yaw, and generate a third signal to control a third function of the medical device based on the determined change in yaw position.

Certain embodiments may provide one or more technical advantages, including improved ergonomics that align to natural movements of the foot. Certain embodiments provide improved control by, for example, facilitating foot-operated commands about three axes centered near the operator's ankle joint, thus responding to natural motion of the foot centered at the ankle. Certain embodiments minimize upper body reaction to foot and leg movements when actuating foot controls, thereby improving stability of the hands and head during a surgical procedure. Certain embodiments improve balance by allowing an operator to maintain his weight resting on the heel during operation of the foot controller, thereby reducing or minimizing weight shift. Certain embodiments may provide more intuitive foot controls and facilitate analog joystick designs that are easier to operate than digital button controls. These and other advantages will be apparent to those skilled in the art in view of the present drawings and specification.

BRIEF DESCRIPTION OF THE DRAWINGS

For a more complete understanding of the present disclosure and the advantages thereof, reference is now made to the following description taken in conjunction with the accompanying drawings in which like reference numerals indicate like features and wherein.

One skilled in the art will understand that the drawings, described below, are for illustration purposes only, and are not intended to limit the scope of applicant's disclosure.

DETAILED DESCRIPTION

The following description is presented to enable one skilled in the art to make and use the inventions disclosed, and is generally provided in the context of a particular application and its requirements. Various modifications to the disclosed embodiments will be apparent to those skilled in the art, and it is understood that general principles set forth herein may be applied to other embodiments and applications without departing from the spirit and scope of the disclosure. It is further understood that systems, devices, components, and methods described with respect to one embodiment may be combined with features, components, and/or steps described with respect to other embodiments. For the sake of brevity, however, the numerous iterations of these combinations will not be described separately. Thus, the scope of the disclosure is not limited to the embodiments described, but is to be accorded the widest scope consistent with the claims.

In general, the present disclosure relates to an ergonomic footswitch with three axes of rotation. Although the axes of rotation may be centered (intersect) at various locations in different embodiments, certain variants provide unique advantages by centering the three axes near the operator's ankle, rather than near the sole of the foot.

Figure 1:
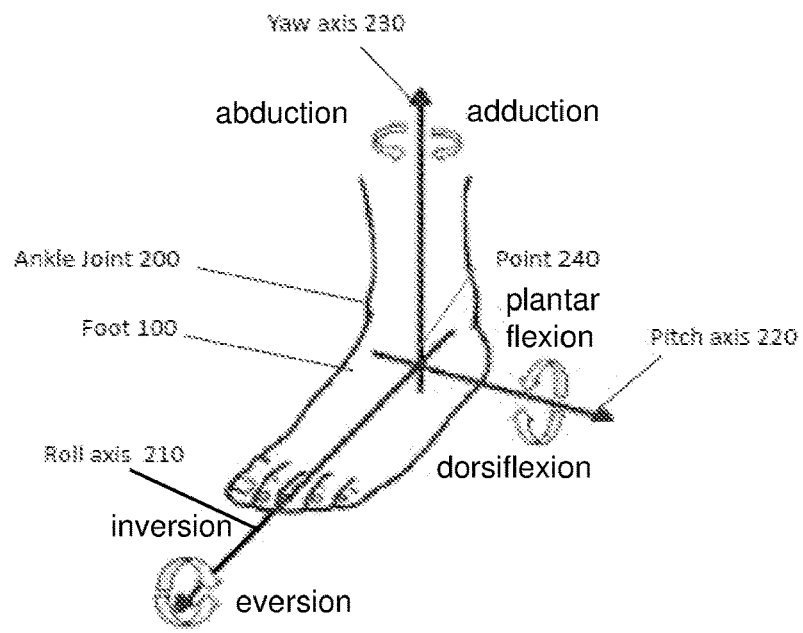
FIG. 1 illustrates natural movements of a foot about three axes centered in the ankle.

FIG. 1 illustrates natural movement of a typical operator's foot 100 about three axes of rotation. Inversion (rotation inward, sole toward midline) and eversion (rotation outward, sole away from midline) of foot 100 occurs about roll axis 210. Plantarflexion (downward movement away from tibia) and dorsiflexion (upward movement towards tibia) of foot 100 occur about a pitch axis 220. Abduction (lateral rotation away from center) and adduction (lateral rotation towards center) of foot 100 occurs about a yaw axis 230 which generally extends Accordingly, foot 100 is capable of tri-plane motion about a point 240 where yaw axis 230, pitch axis 220, and roll axis 210 intersect. This point of intersection lies within ankle joint 200.

Figure 2:
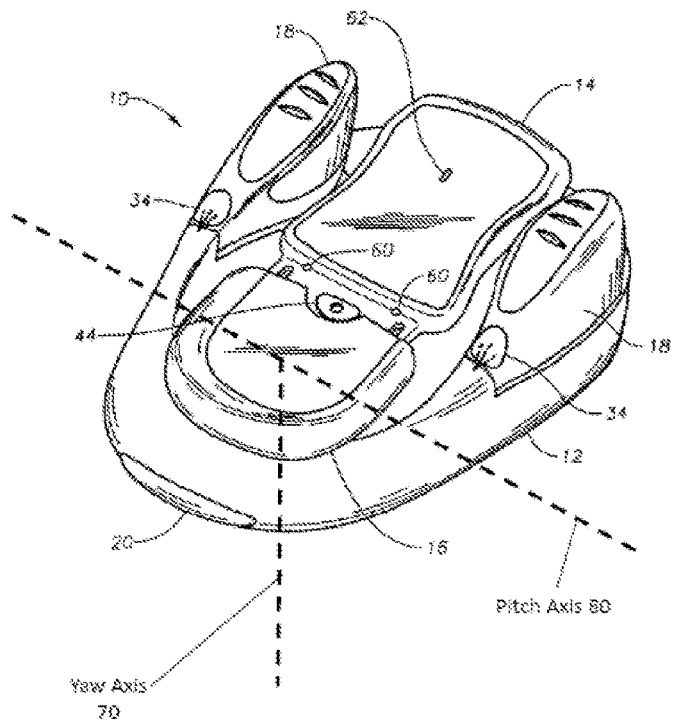
FIG. 2 illustrates aspects of a conventional bi-axial footswitch.

FIG. 2 illustrates basic components of an example a conventional bi-axial footswitch. Footswitch 10 includes base 12, treadle 14 having heel cup 16 and side or wing switches 18, all of which can be made from any suitable material, such as stainless steel, titanium or plastic. Base 12 may contain protective bumper 20 made from a relatively soft elastomeric material. Side switches 18 may be adjusted inwardly or outwardly to increase or decrease the distance between switches 18 and accommodate for variations in the width of a user foot. The relative position of switches 18 may be determined visually by the use of switch position indicators 34. The length of treadle 14 may be adjusted by sliding movement of heel cup 16 and securing it in position using locking lever 44. The relative position of heel cup 16 relative to treadle 14 may be visually indicated by indicators 60. Footswitch 10 supports and responds to commands based on bi-planar foot movements, namely abduction/adduction about a yaw axis and plantarflexion/dorsiflexion about pitch axis 80. Yaw axis 70 and pitch axis 80 intersect at a point near the surface of heel cup 16 where contact is made with an operator's foot.

Figure 3:
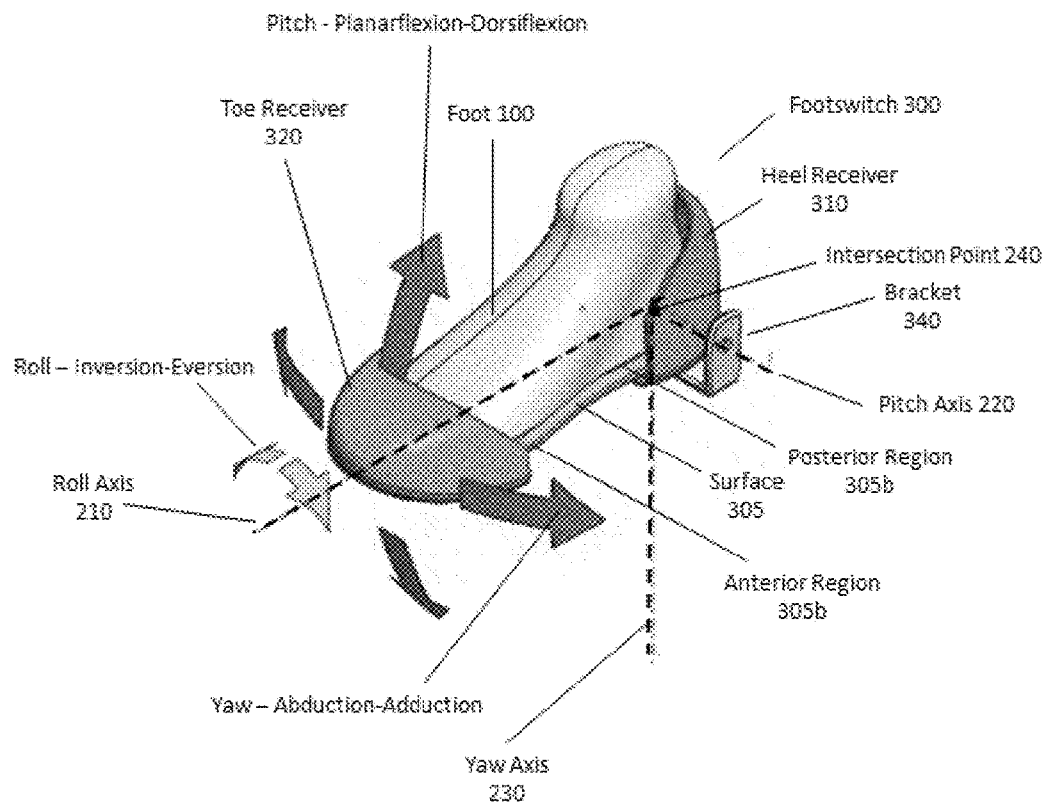
FIG. 3 illustrates aspects of a footswitch, according to certain embodiments.
Figure 4:
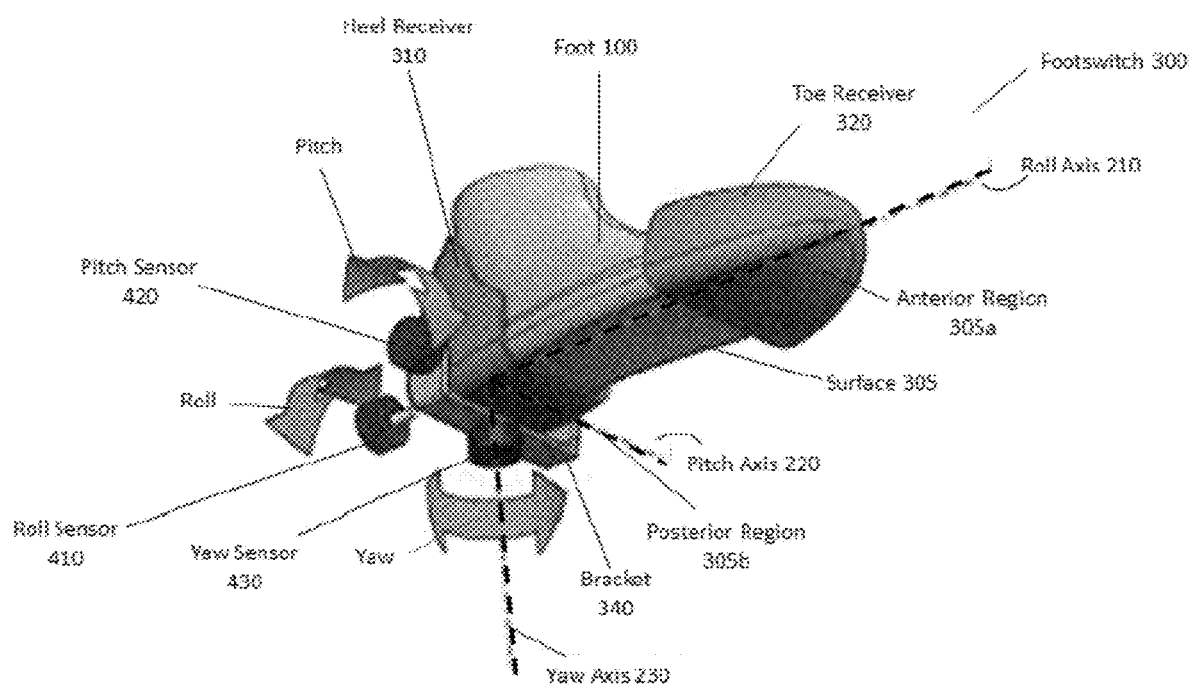
FIG. 4 illustrates aspects of a footswitch, according to certain embodiments.
Figure 5:
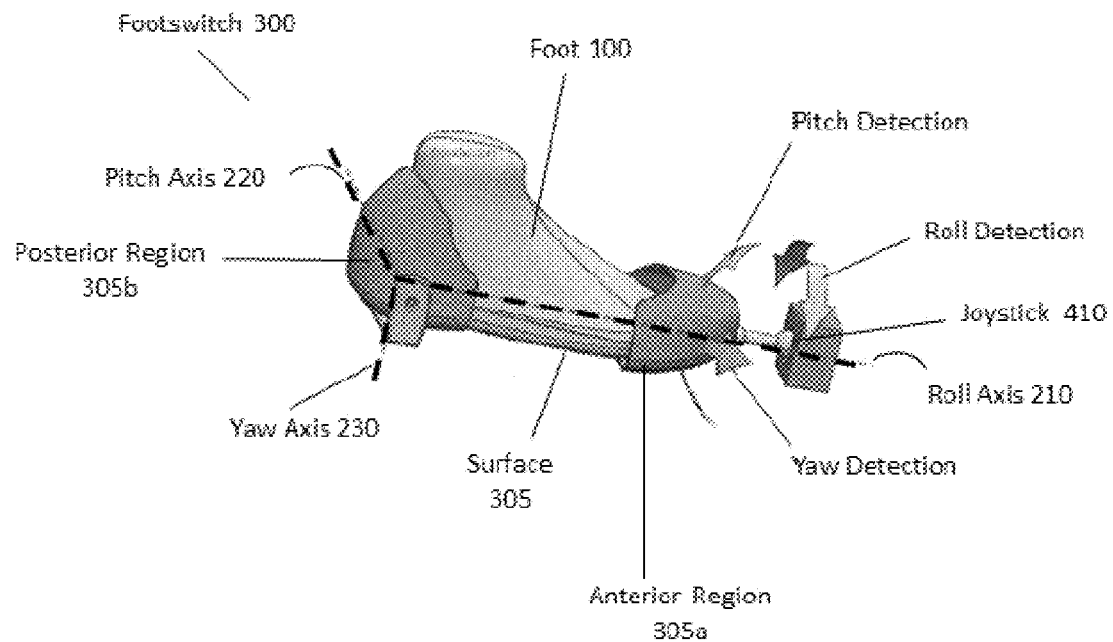
FIG. 5 illustrates aspects of a footswitch, according to certain embodiments.

FIG. 3 illustrates aspects of one embodiment of a footswitch 300 which supports and responds to commands based on natural tri-planar motion of an operator's foot 100 centered near the operator's ankle. It is expressly noted at the outset that the footswitch designs illustrated in FIGS. 3-5 are merely examples provided to explain broader inventive principles and features. The claims are not limited to the footswitch design(s) illustrated in FIGS. 3-5, but should be understood to encompass a broad range of footswitch designs that include at least the claimed features and optionally include other features, such as switches, buttons, locking and adjustment mechanisms, and the like.

Returning to FIG. 3, switch 300 includes a movable surface 305 configured to contact and engage with an operator's foot 100. Surface 305 comprises an anterior region 305a to contact the front (toe region) of foot 100 and a posterior region 305b to contact the rear (heel region) of foot 100.

In certain embodiments, anterior and posterior regions 305a and 305b may be part of an integral structural plate or pedal. In other embodiments, anterior and posterior regions 305a and 305b may be separate structural pieces. For example, a posterior region 205b may comprise a heel rest, heel cup, and/or heel receiver 310. Anterior region 205a may comprise a pedal, treadle, plate, and/or toe receiver 320. All or portions of surface 305 may be generally flat or contoured to accommodate a foot shape, and may be made of any suitable materials, such as metal (e.g., stainless steel, titanium), plastic, or rubber. Various examples of surface 305 are described and illustrated in U.S. Pat. Nos. 6,862,951, 7,185,555, and 7,626,132 which are incorporated herein by reference. It is again noted that the particular structural features shown in FIG. 3 are specific to example embodiments, and one skilled in the art will appreciate that various additional or alternative structures may be used in other embodiments, consistent with the disclosure and claims.

Surface 305 may be coupled to a base or body to support footswitch 300 on a horizontal surface such as an operating room floor. Various examples of bases are described and illustrated in U.S. Pat. Nos. 6,862,951, 7,185,555, and 7,626,132. The base may surround all or part(s) of surface 305 and provide support to foot 100 to maintain secure contact during operation. The base may be weighted and shaped to provide a secure interface to the operating room floor and may be made of any suitable materials including metal (e.g., stainless steel, titanium), plastic, or rubber. The bottom of the base may be coated or inlaid with a high-friction material (e.g., a polymer such as VERSAFLEX TPE). Aspects of surface 305 and/or the base may be adjustable in size and position to accommodate the particular foot or shoe shape/size of an operator.

Surface 305 may be coupled to the base so as to facilitate movement about three axes of rotation: roll axis 210, pitch axis 220, and yaw axis 230. In particular, all or part of movable contact surface 305 may be configured to roll about roll axis 210 in response to inversion or eversion of foot 100 engaged with surface 305, pitch about a pitch axis 220 in response to plantarflexion or dorsiflexion of foot 100, and yaw about a yaw axis in response to abduction or adduction of foot 100. In other embodiments, surface 305 may be coupled to the base so as to facilitate movement about two axes of rotation (e.g., roll+pitch, roll+yaw, pitch+yaw). In certain embodiments, a system operator may configure footswitch 300 to activate or disable one or more axes of rotation prior to a particular procedure.

Roll axis 210, pitch axis 220, and yaw axis 230 may or may not be perpendicular in various embodiments. In some examples, the orientation and relative angles of roll axis 210, pitch axis 220, and yaw axis 230 may reflect the natural axes of movement of the ankle. One skilled in the art will appreciate that physiological and anatomical features and movements of the foot and ankle are set forth in relevant scientific literature and are not reproduced here for brevity.

Surface 305 may be movably coupled to the base so that the two or three axes of rotation intersect at a point above surface 305, such as in an ankle region of foot 100. Conventional footswitches may rotate about one or two axes of movement, but the movement axes intersect below around surface 305 near the sole of foot 100. However, the natural axes of rotation of the foot are aligned through the ankle (as shown in FIG. 1), not the sole or floor. Accordingly, footswitch 300 is designed so that movement of surface 305 occurs about two or three axes which intersect above (superior to) surface 305, such as in or near the operator's ankle. In this respect, embodiments provide bi- or tri-axial movement about axes aligned in a position elevated with respect to prior switches. This aspect may provide several benefits, including improved ergonomics and reduced upper body movement during operation of footswitch 300.

Accordingly, in certain variants footswitch 300 is designed and constructed so that roll axis 210 of surface 305 is in a roll plane which is superior to (above) surface 305 (that is, closer to the operator's upper leg when the foot is resting of surface 305). In certain variants, surface 305 is coupled to a base so that roll axis 210, pitch axis 220, and yaw axis 320 intersect at a point 240 which is superior to surface 305. For example, point 240 may be located between 1-30 millimeters (mm), 2-25 mm, or 5-20 mm above surface 305. In certain embodiments, point 240 corresponds to a point where the frontal, sagittal, and transverse planes of foot 100 intersect. For example, point 240 may be located within 10 mm, 5 mm, 2.5 mm, or 1 mm of the intersection of the frontal, sagittal, and transverse planes of a typical foot 100. In certain variants, the location of point 240 may be adjustable to accommodate the size and shape of a particular user, so that point 240 may be fixed at a location within 10 mm, 5 mm, 2.5 mm, or 1 mm of the intersection of the frontal, sagittal, and transverse planes of an actual operator's foot.

Surface 305 may be movably coupled to the base at one or more points using any suitable combination of springs and return springs, rings, rods, wheels, gears, chains, belts, pulleys, rods, arms, bearings, dampers, alignment caps, screws, and the like to facilitate independent movement about each axis 210, 220, and 230. In certain embodiments, surface 305 is movably coupled to a base which includes bracket 340, which may define an opening corresponding to pitch axis 220. Return springs may be used to provide for automatic reentering or biasing of surface 305 to a neutral position before and following rotation about any of axes 210, 220, or 230. Springs and dampers may be used to provide a combination of pushing and pulling forces to provide resistance and "feel" during rotation about any of the axes, and to assist with maintaining the foot 100 in a particular position (rotated about any or all of the axes) with comfort.

FIG. 4 illustrates an embodiment of footswitch 300 which includes sensors coupled to surface 305 and/or the base to independently detect movement about three axes (e.g., acceleration, velocity, change in position, etc.). In this example, footswitch 300 includes a roll sensor 410 configured to detect a roll of contact surface 305 about roll axis 210 and send a signal indicating the detected roll to a surgical system controller (e.g., microprocessor and memory configured to execute software controlling tools or properties of a surgical system), a pitch sensor 420 configured to detect a pitch of contact surface 305 about pitch axis 220 and send a signal indicating the detected pitch to the surgical system controller, and a yaw sensor 430 configured to detect a yaw of contact surface 305 about yaw axis 230 and send a signal indicating the detected yaw to the surgical system controller. Sensors 410, 420, and 430 may comprise any suitable analog, digital, hardware, or software-based sensors, including one or more accelerometers, gyroscopes, compasses, rotary position sensors, tilt sensors, angular sensors, cameras, proximity sensors, CMOS sensors, pressure sensors, and the like. A description of example pressure sensors is set forth in Provisional Application No. 62/423,272 titled "Ergonomic Foot-Operated Joystick", filed Nov. 17, 2016, the disclosure of which is incorporated by reference herein in its entirety. In certain embodiments, sensors 410, 420, and 430 may be situated around posterior region 305b of surface 305. For example, FIG. 3 depicts sensors 410, 420, and 430 coupled to bracket 340, which is in turn coupled to posterior region 305b of surface 305. One skilled in the art will appreciate that various alternative sensor configurations are within the scope of the disclosure.

FIG. 5 illustrates a configuration of footswitch 300, according to certain embodiments. In particular, embodiments may include a joystick 410 which includes sensors configured to detect pitch, roll, and/or yaw of surface 305. Joystick 410 may be arranged and coupled to footswitch 300 in any suitable location, including anterior region 305a of surface 305. In various embodiments, roll axis 210, pitch axis 220, and yaw axis 320 may intersect at point 240 near the operator's ankle, as shown in FIG. 3. In certain variants, the location of point 240 may be fixed or adjustable to accommodate the size and shape of a particular user, so that point 240 may be fixed at a location within 10 mm, 5 mm, 2.5 mm, or 1 mm superior to surface 305.

Figure 6:
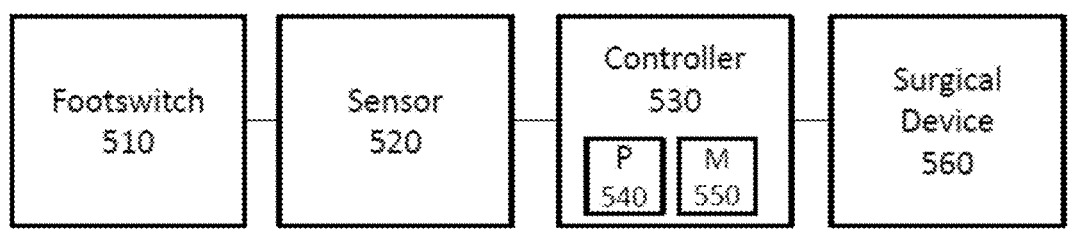
FIG. 6 illustrates components of a surgical device system, according to certain embodiments.

FIG. 6 illustrates a block diagram of a footswitch control system, according to certain embodiments. Footswitch 510 may comprise any suitable footswitch, including but not limited to footswitch 300 shown in FIGS. 2-4. In certain embodiments, footswitch 510 comprises a bi-axial footswitch configured to pitch and yaw, roll and yaw, and/or pitch and roll about axes which intersect at a point corresponding to the ankle of an operator. In certain embodiments, footswitch 510 comprises a tri-axial footswitch configured to pitch, yaw, and roll about three axes which intersect at a point corresponding to the ankle of an operator.

One or more sensors 520 are coupled to footswitch 510 to detect axial movement and generate signals indicating detected axial movement for transmission to a system controller 530. Sensors 520 may comprise any suitable analog, digital, hardware, or software-based sensors, including one or more accelerometers, gyroscopes, compasses, rotary position sensors, tilt sensors, angular sensors, and the like. In certain embodiments, sensor 520 includes but is not limited to roll sensor 410, pitch sensor 420, and yaw sensor 430.

Controller 530 comprises a processor 540 and memory 550. Processor 540 may comprise a microprocessor, CPU, ASIC, or other computing component. Memory 550 may comprise a non-transitory computer-readable medium configured to store instructions executable by processor 540 to receive signals from sensors 520, interpret the received signals, and generate commands to control components or characteristics of a surgical device 560. For example, processor 540 may execute instructions which receive signals from sensor 510 indicating uni-axial, bi-axial, or tri-axial movement of footswitch 300, compare received signals to predetermined or preconfigured control settings to identify an intended consequence of the axial movement, and generate a command signal to control imaging, light, fluid flow, suction, rotation, and/or focus features of surgical device 560. Software stored in memory 550 may comprise instructions to perform the described features using any appropriate combination of methods, functions, routines, and programs.

In certain embodiments, a different function of a medical device is controlled by different movements. For example, controller 530 may be programmed so that detecting inversion or eversion of the foot (causing the contact surface to roll about a roll axis) initiates a command to control a first function of a medical device 560, detecting plantarflexion or dorsiflexion of the foot (causing the contact surface to pitch about a pitch axis) initiates a command to control a second function of the medical device 560, and detecting abduction or adduction of the foot (causing the contact surface to yaw about a yaw axis) initiates a command to control a third function of the medical device 560.

In certain embodiments, controller 650 includes a non-transitory computer-readable medium (e.g., memory 550) storing instructions that, when executed, cause processor 540 to receive a signal (e.g., from one or more sensors 520) indicating a roll about a roll axis of a contact surface of a foot-operated controller, determine a change in roll position associated with the roll, and generate a first signal to control a first function of a device 560 based on the determined change in roll position. The instructions, when executed, may further cause the processor to receive a signal (e.g., from one or more sensors 520) indicating a pitch about a pitch axis of the contact surface of the foot-operated controller, determine a change in pitch position associated with the pitch, and generate a second signal to control a second function of the device 560 based on the determined change in pitch position. The instructions, when executed, may further cause the processor to receive a signal (e.g., from one or more sensors 520) indicating a yaw about a yaw axis of the contact surface of the foot-operated controller, determine a change in yaw position associated with the yaw, and generate a third signal to control a third function of the device 560 based on the determined change in yaw position.

Device 560 may be any surgical system, including but not limited to ophthalmic surgical systems such as the LENSX® Laser System, WAVELIGHT® Laser System, CENTURION® Vision System, or CONSTELLATION® Vision Systems manufactured by Alcon®. In other embodiments, device may be a non-surgical device, including a vehicle, a laser, or manufacturing equipment, for example.

Figure 7:
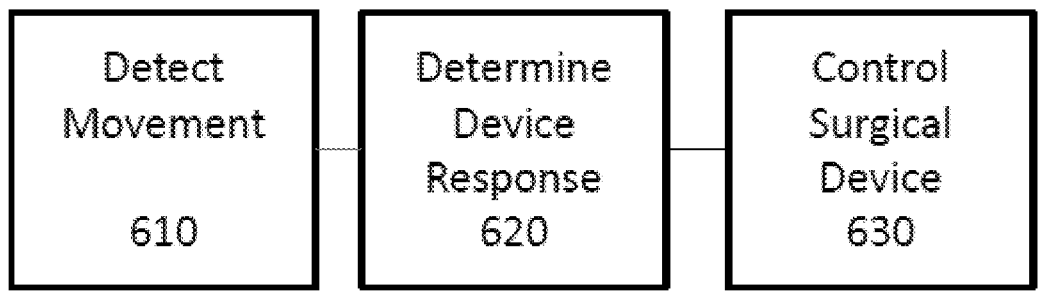
FIG. 7 illustrates a method of controlling a footswitch, according to certain embodiments.

FIG. 7 illustrates a method performed by certain embodiments of footswitch 510. At step 610, a sensor system (e.g. sensor 520) associated with footswitch 510 may detect movement of footswitch 300. For example, one or more sensors may detect a surface or section of footswitch 300 rolling about a roll axis in response to inversion or eversion of a foot engaged with the contact surface, pitching about a pitch axis in response to plantarflexion or dorsiflexion of the foot, and/or yawing about a yaw axis in response to abduction or adduction of the foot. The sensors 520 may send a signal indicating the detected movement to controller 530.

At step 620, processor 540 may execute instructions stored in memory 550 to determine the appropriate response of a surgical device 560 in response to the detected signals. The appropriate response may be pre-stored in memory of a surgical device 560 or footswitch 510, or may be configured by a system operator using a user interface of device 560 prior to the procedure. For example, the appropriate response to detected rolling, pitching, or yawing may be modifying imaging, light, fluid flow, suction, rotation, and/or focus characteristics of surgical device 560. In certain embodiments, controller 530 may account for the rate of change and/or magnitude of any detected rolling, pitching, or yawing in determining the appropriate response.

At step 630, processor 540 may execute instructions stored in memory 550 send command signals to surgical device 560, thereby controlling the device to implement the determined response.

Figure 8:
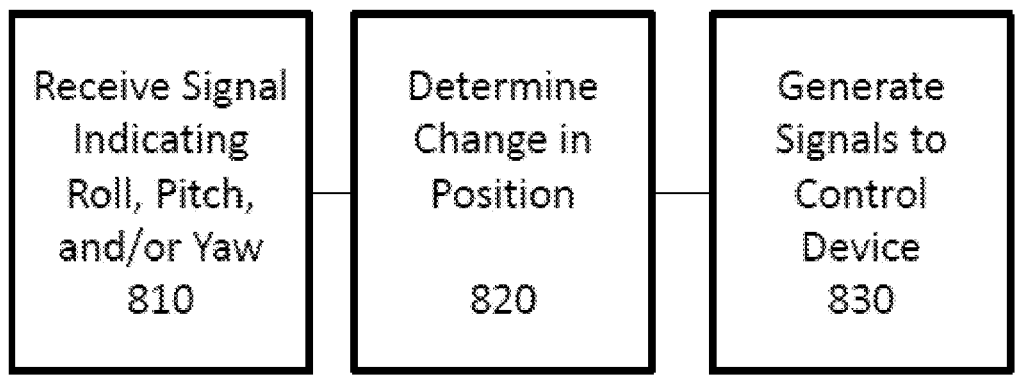
FIG. 8 illustrates a method performed by software for a footswitch, according to certain embodiments.

FIG. 8 illustrates a method performed by software for a footswitch, according to certain embodiments. At step 810, a device controller comprising a processor 540 executing software stored on a non-transitory computer-readable medium 550 receives a signal from a footswitch component (e.g., one or more footswitch sensors) indicating that the footswitch (or one or more components thereof, such as a footplate surface) moved about one or more axes. The signal may indicate, for example, changes in yaw, pitch, or roll, and may further indicate a sign (direction), magnitude, velocity, and/or of such change. Alternatively or additionally, a sign (direction), magnitude, velocity, and/or rate of change of the pitch, roll and/or yaw movement may be determined by the processor 540 executing software which compares received signal inputs against prior signal inputs, in real time.

For example, software of the device controller 530 may store initialized and/or prior position data for the footswitch in memory, compare received signals with the stored data, and calculate a change in position of the footswitch in real time based on the comparison. At step 820, for example, processor 540 may execute one software function or routine to determine the a change in position by comparing a received signal indicating a current yaw, pitch, and/or roll position to data associated with prior signals stored in memory 550 indicating prior yaw, pitch, and/or roll positions, and then calculating a change or difference based on the received signal and stored data. The software routines may transform or convert raw signal data into a suitable data format prior to the comparison and/or storage.

At step 830, processor 540 may further execute instructions to generate signals to control a device based on the determined change in position. For example, processor 540 may execute software which correlates and/or translates footswitch position data with changes to specified device functions based on default or user-configured settings. For example, prior to a procedure, a system operator may input settings instructing footswitch software to modify a device flow rate based on pitch position, illumination based on yaw position, and guidance visualization based on a roll position. Any particular axial movement may be configured to control or modify (e.g., increase/decrease, activate/deactivate, enhance/reduce, scroll, shift, zoom, select, engage, etc.) any applicable device function.

It will be appreciated that several of the above-disclosed and other features and functions, or alternatives thereof, may be desirably combined into many other different systems or applications in various embodiments. It will also be appreciated that various presently unforeseen or unanticipated alternatives, modifications, variations or improvements therein may be subsequently made by those skilled in the art which alternatives, variations and improvements are also intended to be encompassed by the following claims.

What is claimed is:

1. A foot-operated controller, comprising:
a base configured to rest on a floor surface;
a movable contact surface coupled to the base, the movable contact surface comprising an anterior region to support a toe region and a posterior region to support a heel region, the movable contact surface configured to:
roll about a roll axis in response to inversion or eversion of a foot engaged with the contact surface;
pitch about a pitch axis in response to plantarflexion or dorsiflexion of the foot; and
yaw about a yaw axis in response to abduction or adduction of the foot;
a roll sensor coupled to the foot-operated controller and configured to detect a roll of the contact surface and send a signal indicating the detected roll to a microprocessor;
a pitch sensor communicatively coupled to the foot-operated controller and configured to detect a pitch of the contact surface and send a signal indicating the detected pitch to the microprocessor; and
a yaw sensor communicatively coupled to the foot-operated controller and configured to detect a yaw of the contact surface and send a signal indicating the detected yaw to the microprocessor
wherein the roll axis is located in a roll plane superior to the contact surface;
wherein the roll, pitch and yaw axes intersect at a point aligned with an ankle moving the foot.

2. The controller of claim 1, wherein the roll, pitch and yaw axes intersect at a point located 1-30 millimeters above the contact surface.

3. The controller of claim 1, wherein a point at which the roll, pitch, and yaw axes intersect is adjustable.

4. A foot-operated controller, comprising:
a base configured to rest on a floor surface;
a movable contact surface coupled to the base, the movable contact surface comprising an anterior region to support a toe region and a posterior region to support a heel region, the movable contact surface configured to:
roll about a roll axis in response to inversion or eversion of a foot engaged with the contact surface;
pitch about a pitch axis in response to plantarflexion or dorsiflexion of the foot and
yaw about a yaw axis in response to abduction or adduction of the foot a roll sensor coupled to the foot-operated controller and configured to detect a roll of the contact surface and send a signal indicating the detected roll to a microprocessor;
a pitch sensor communicatively coupled to the foot-operated controller and configured to detect a pitch of the contact surface and send a signal indicating the detected pitch to the microprocessor; and
a yaw sensor communicatively coupled to the foot-operated controller and configured to detect a yaw of the contact surface and send a signal indicating the detected yaw to the microprocessor;
wherein the roll, pitch and yaw axes intersect at a point superior to the contact surface.

5. A foot-operated controller, comprising:
a base configured to rest on a floor surface;
a movable contact surface coupled to the base, the movable contact surface comprising an anterior region to support a toe region and a posterior region to support a heel region, the movable contact surface configured to:
roll about a roll axis in response to inversion or eversion of a foot engaged with the contact surface;
pitch about a pitch axis in response to plantarflexion or dorsiflexion of the foot and
yaw about a yaw axis in response to abduction or adduction of the foot
a roll sensor coupled to the foot-operated controller and configured to detect a roll of the contact surface and send a signal indicating the detected roll to a microprocessor;
a pitch sensor communicatively coupled to the foot-operated controller and configured to detect a pitch of the contact surface and send a signal indicating the detected pitch to the microprocessor; and
a yaw sensor communicatively coupled to the foot-operated controller and configured to detect a yaw of the contact surface and send a signal indicating the detected yaw to the microprocessor;
wherein the roll sensor, pitch sensor, and yaw sensor each comprises one or more pressure sensors.

* * * * *